United States Patent
Dresty, Jr. et al.

(10) Patent No.: US 6,641,739 B2
(45) Date of Patent: Nov. 4, 2003

(54) PROCESS OF FORMING AN OXIDIZING AGENT IN LIQUID BY USE OF RINGING MAGNETIC FLUX

(75) Inventors: John Edward Dresty, Jr., South Glastonbury, CT (US); Dennis John Opheim, Cheshire, CT (US)

(73) Assignee: Clearwater Systems, LLC, Essex, CT (US)

( * ) Notice: Subject to any disclaimer, the term of this patent is extended or adjusted under 35 U.S.C. 154(b) by 12 days.

(21) Appl. No.: 10/021,962

(22) Filed: Dec. 14, 2001

(65) Prior Publication Data

US 2003/0111420 A1 Jun. 19, 2003

(51) Int. Cl.$^7$ .................................................. C02F 1/48
(52) U.S. Cl. ........................ 210/695; 204/554; 165/108; 422/22; 210/748; 210/759; 210/764
(58) Field of Search ................................ 210/143, 222, 210/223, 243, 695, 748, 749, 758, 759, 764; 204/554, 555, 560, 660, 661, 663, 165; 422/186.01, 186.02, 186.03, 22, 28; 261/DIG. 11; 165/108, 132

(56) References Cited

U.S. PATENT DOCUMENTS

| | | | | |
|---|---|---|---|---|
| 4,954,263 A | * | 9/1990 | Woodhouse | |
| 5,407,637 A | * | 4/1995 | Gibbone et al. | ............... 422/22 |
| 5,679,257 A | * | 10/1997 | Coate et al. | ................ 210/695 |
| 5,702,600 A | | 12/1997 | Pandolfo | ................... 210/222 |
| 6,063,267 A | | 5/2000 | Crewson et al. | ............ 210/143 |

OTHER PUBLICATIONS

John Lane et al., "Non–Chemical Water Treatment In Cooling Towers" Feb. 2000.
Opheim, Dennis J., "The Effect of Pulse–Power Technology on the Microbial Content and Biofilm Formation in Evaporative Cooling Towers", 100th Annual General Meeting of The American Society of Microbiology, May 21–25, 2000, 3 pgs., Los Angeles, CA. (www.clearwater–dolphin.com).
"Non–Chemical Water Conditioning at Schick: A Pollution Prevention Case Study", CT DEP Case Study, 3 pgs. (www-.clearwater–dolphin.com), Undated.
Method of Action, 3 pgs, (www.clearwater–dolphin.com), Undated.
"Kinetics of Microbial Inactivation for Alternative Food Processing Technologies Oscillating Magnetic Fields", U.S. Food and Drug Administration Center for Food Safety and Applied Nutrition, Jun. 2, 2000, pp. 1–9.
Encyclopedia of Chemical Technology, fourth edition, Kirk–Othmer, vol. 13, Helium Group to Hynotics, Undated.
Costerson, J.W. and Steward, Philip S., "Battling Iofilms", Scientific American, Jul. 2001, pp. 75–81.
"Operation, Installation, and Maintenance on The Dolphin Hytronic Series 1000", Clearwater Technical Manual, Clearwater Systems LLC, Essex, CT 06426, Undated.
Hua, Inez: "An Investigation f Homogenous and Heterogeneous Sonochemistry for Destruction of Hazardous Waste", Environmental Management Science Program, Jun. 1, 1998, Project ID No. 54834, Purdue University, pp. 3.
Schwikkard, G.W. et al.: "Design of a Sonochemical Reactor", Pollution Research Group, Department of Chemical Engineering, pp. 1, Undated.
Colic, M. et al.: "Mechanism of the Long–Term Effects of Electromagnetic Radiation on Solutions and Suspended Colloids", Languir 1998, vol. 14, pp. 783–787.

* cited by examiner

*Primary Examiner*—Joseph Drodge
(74) *Attorney, Agent, or Firm*—McCormick, Paulding & Huber LLP

(57) ABSTRACT

A method of making an oxygen-rich and stabilized oxidizing agent in a liquid, preferably water, involves exposure of aerated liquid to repeated bursts of ringing magnetic flux having a primary frequency of 10 kHz to 80 kHz, with the bursts repeated at a frequency of 1 Hz to 100 Hz, and with the water being kept basic at a pH level between pH 7 to pH 10. The oxidizing agent is believed to be a relatively stable complex of hydrogen peroxide, and has a significant antimicrobial effect on microorganisms, including biofilms, in the water achieved by oxidation of the oxidizing agent with chemical components of the microorganisms.

16 Claims, 3 Drawing Sheets

PROCESS OF FORMING AN OXIDIZING AGENT IN LIQUID BY USE OF RINGING MAGNETIC FLUX

BACKGROUND OF THE INVENTION

1. Field of the Invention

This invention relates to the field of liquid treatment and purification and, in particular, to a method of treating a liquid with a ringing magnetic flux whereby an oxidizing agent having prolonged effectiveness is formed and stabilized in the liquid. The method of the present invention may be used for the treatment of any liquid where biocidal and or biostatic activity is needed and is particularly suited to the treatment of water containing undesired bacteria and/or other microorganisms.

2. Description of Related Art

Various attempts and investigations have been made in the past in respect to the possible use of static and/or time varying magnetic field for the purpose of reducing or eliminating undesirable effects of microbes in various solids and liquids. For example, a summary of various known methods using static and/or time varying magnetic fields for the treatment of food products is given in an article entitled "Kinetics of Microbial Inactivation for Alternative Food Processing Technologies—Oscillating Magnetic Fields", issued by the U.S. Food and Drug Administration, Center for Food Safety and Applied Nutrition, under date of Jun. 2, 2000. In the various methods described by this article the general effect of the magnetic fields is taken to be that of having some sort of mechanical effect on the target microorganisms, such as mechanical disruption of cell structure so as to either kill cells or to impair their vitality and reproductive capacity.

In the past, Clearwater Systems, LLC, the assignee of this application, has manufactured and sold a device for use in magnetically treating liquids, which device is the subject of U.S. Pat. No. 6,063,267 and is sold under the trademark "Dolphin". As originally conceived, the Dolphin device was seen to be one primarily for use in treating water to prevent the depositing of scale onto the walls of pipes, tanks and other equipment handling water in both domestic and industrial situations, instead causing the minerals to form power in the bulk solution, and it was also seen to have an antimicrobial effect by way of causing microorganisms to become encapsulated in shells of the mineral powder formed in lieu of the mineral scale.

In more detail, the past known effect of the Dolphin device for the control of microorganisms in water was related to the Dolphin device causing the precipitation of calcium carbonate and other dissolved minerals in the water to form crystals or proto-crystals of calcite/aragonite and vaterite or the like. As these crystals or proto-crystals grow and aggregate with one another, under the influence of the oscillating magnetic flux produced by the Dolphin device, they also combine, primarily non-chemically, with the microorganisms in the water, thereby encapsulating the microorganisms with the material of the crystals or proto-crystals and in this way kill the microorganisms or at least inhibit their reproduction and growth.

As the result of recent work and further investigation in respect to the Dolphin device, Applicants have discovered that, under certain conditions, the treatment of liquids by ringing magnetic flux of the type produced by the Dolphin device has a further previously unrecognized and unanticipated effect on controlling microbial activity in the treated liquid. That is, Applicants have discovered that the bursts of ringing magnetic flux created by the Dolphin device not only are beneficial in reducing or eliminating scale deposits and encapsulating microbes in precipitated mineral material, but also, under certain conditions of operation, can produce a stabilized oxidizing agent in the water, which oxidizing agent then chemically reacts with microorganisms by oxidizing components of the cell structure to either quickly kill the microorganisms or to at least creating sub-lethal injury that reduces microorganism population. The exact nature of the oxidizing agent is not yet known in full detail, but Applicants strongly believe it to be a stabilized form of hydrogen peroxide, as explained in more detail hereinafter.

Hydrogen peroxide is a known oxidizing agent which has favorable anti-microbial activity with decomposition products comprising water and oxygen (i.e., harmless byproducts) making it ideal for water treatment or water purification systems. However, the previous use of hydrogen peroxide and other oxidizing agents in water treatment systems has been costly and troublesome since the oxidizing agent is generally added to the water in question as a separate purchased product. This aspect makes these prior art water treatment systems expensive and difficult. Further, when pure hydrogen peroxide is added in batch doses to water or other liquid it quickly decomposes before it can effectively oxidize microorganisms, and it does not become uniformly or homogeneously distributed throughout the concerned body of liquid. Thus, it would be beneficial to provide a way much simpler, less costly, and better able to obtain a uniform distribution of hydrogen peroxide for treating water with hydrogen peroxide or similar oxidizing agent.

The use of hydrogen peroxide to treat biofilms also has great utility in water treatment systems. Biofilms of bacteria can reside and colonize in pipes, and are particularly prevalent and of concern in the open-loop water circuit of air conditioning system cooling towers. They have been heretofore difficult to eradicate given the complex matrix in which the bacteria reside such that anti-microbial agents have difficulty penetrating the matrix. Some known water treatment systems concentrate on scale removal and encapsulation of bacteria in the water. However, given the biofilm matrix, encapsulation of the individual bacteria is nearly impossible. Thus, it would be advantageous to provide a water treatment system which can treat and prevent biofilms utilizing a stabilized form of hydrogen peroxide or other oxygen-rich oxidizing agents. By "stabilized" it is meant that the hydrogen peroxide or other oxidizing agent is not in an unstable pure form but instead is in a more stable form, in which it has complexed with compounds or ions inherent in the water, allowing its concentration to be gradually increased as the water or other liquid is recirculated past a treatment zone with the concentration becoming uniform throughout the whole body of treated liquid.

Bearing in mind the problems and deficiencies of the prior art, it is therefore an object of the present invention to provide a simple method and means of generating stabilized hydrogen peroxide or other oxygen-rich oxidizing agent for liquid treatment and purification.

It is another object of the present invention to provide a method of generating stabilized hydrogen peroxide or other oxygen-rich agent to destroy and/or inhibit the growth of biofilms in water and other liquids.

Still other objects and advantages of the invention will be apparent from the following specification.

SUMMARY OF THE INVENTION

The above and other objects and advantages, which will be apparent to one of skill in the art, are achieved in the present invention which is directed to, in a first aspect, a method of generating an oxidizing agent in a treated water based liquid, the method comprising the steps of: providing a magnetic field in the form of successive bursts of ringing magnetic flux; exposing a liquid to the magnetic field for a period sufficient to form an oxidizing agent in the liquid; and maintaining a pH of between 7 to 10, preferably 8 to 9, in the liquid to stabilize the oxidizing agent. Preferably, in the step of exposing a liquid to the flux, the liquid comprises water and the oxidizing agent formed comprises hydrogen peroxide. For convenience, hereinafter the treated liquid will be taken to be water, and the produced oxidizing agent will be taken to be hydrogen peroxide, but the invention, at least in its broader aspects, is not limited to water and hydrogen peroxide.

The method further includes the step of continuing to expose the water to the magnetic flux, preferably by continuously recirculating portions of the water body through the treatment zone, so that the stabilized hydrogen peroxide agent accumulates uniformly in the water. It is also required that a significant amount of dissolved oxygen be in the water which passes through the treatment zone, and preferably this is achieved by aerating the water after it is taken from the main body of water, for recirculation purposes, and either before or after passing through the magnetic field treatment zone. Where the water application is that of use in a cooling tower the aeration may, and preferably does, occur during normal operation of the cooling tower when recirculated water passes over the evaporative surfaces of the cooling tower in the presence of ambient air. The ringing magnetic flux occurs in successive periods with flux oscillations during a ringing period being of a primary frequency between 10 kHz and 80 kHz, plus harmonics, and with the ringing period being repeated at a frequency of between 1 Hz to 100 Hz, and preferably of between 50 Hz to 60 Hz.

In another aspect, the present invention is directed to a method of forming an oxidizing agent in water comprising the steps of: aerating the water; providing a means in close proximity to the water for inducing bursts of ringing magnetic flux in the water having a frequency of 10 kHz to 80 kHz during each burst wherein the bursts are repeated at a frequency of 1 Hz to 100 Hz, preferably 50 Hz to 60 Hz, exposing the water to the bursts of ringing magnetic flux for a time sufficient to form a significant amount of oxidizing agent in the water; and maintaining the water body at a pH of about 7 to 10, preferably 8 to 9, to stabilize the oxidizing agent.

In yet another aspect, the present invention is directed to a method of making hydrogen peroxide or a complex thereof in water, the method comprising the steps of: providing a water source; providing a ringing magnetic flux in close proximity to the water source; exposing the water source to the ringing magnetic flux for a sufficient number of repetitive passes through the ringing flux to form stabilized hydrogen peroxide or a complex thereof in the water; and maintaining a pH of about 7 to 10, preferably 8 to 9, to stabilize the hydrogen peroxide or complex thereof. The water source may be that of a cooling tower. In the step of providing a ringing magnetic flux, the ringing magnetic flux has a frequency of 10 kHz to 80 kHz, plus harmonics, during each ringing period, and the ringing periods repeat at a frequency of 1 Hz to 100 Hz, preferably 50 Hz to 60 Hz. The means for producing the ringing magnetic flux may comprise an inductor or set of inductors in close proximity to the water; a power supply source electrically connected to the inductor or set of inductors having a frequency of 10 kHz to 80 kHz; and a switch in series with the inductor or set of inductors and the power supply source, with an associated controller for the switch alternately opening and closing the switch at a rate of 1 Hz to 100 Hz, preferably 50 Hz to 60 Hz, to provide a succession of ringing periods of magnetic flux passing through the water.

In still another aspect, the present invention is applied to specifically treating water in an air conditioning system cooling tower having an inlet and outlet for water to recirculate water from a maintained body of water through the cooling tower. In this case, the recirculated water is exposed, at a treatment zone, to the bursts of ringing magnetic flux during its recirculation, either before or after its flowing through the water evaporation portion of the cooling tower, to maintain a significant level of dissolved oxygen in the water.

In all embodiments of the inventive method the step of forming an oxidizing agent in the treated water is one wherein the hydrogen peroxide or other oxidizing agent generated is of a stabilized form which does not quickly lose its biocidal and/or biostatic properties and which therefore increases in concentration, homogeneously throughout the body of water, to a desired level as portions of the water body are re-circulated through the magnetic flux treatment zone.

BRIEF DESCRIPTION OF THE DRAWINGS

The drawings forming a part of this application are.

DESCRIPTION OF THE PREFERRED EMBODIMENT(S)

Figure 1:
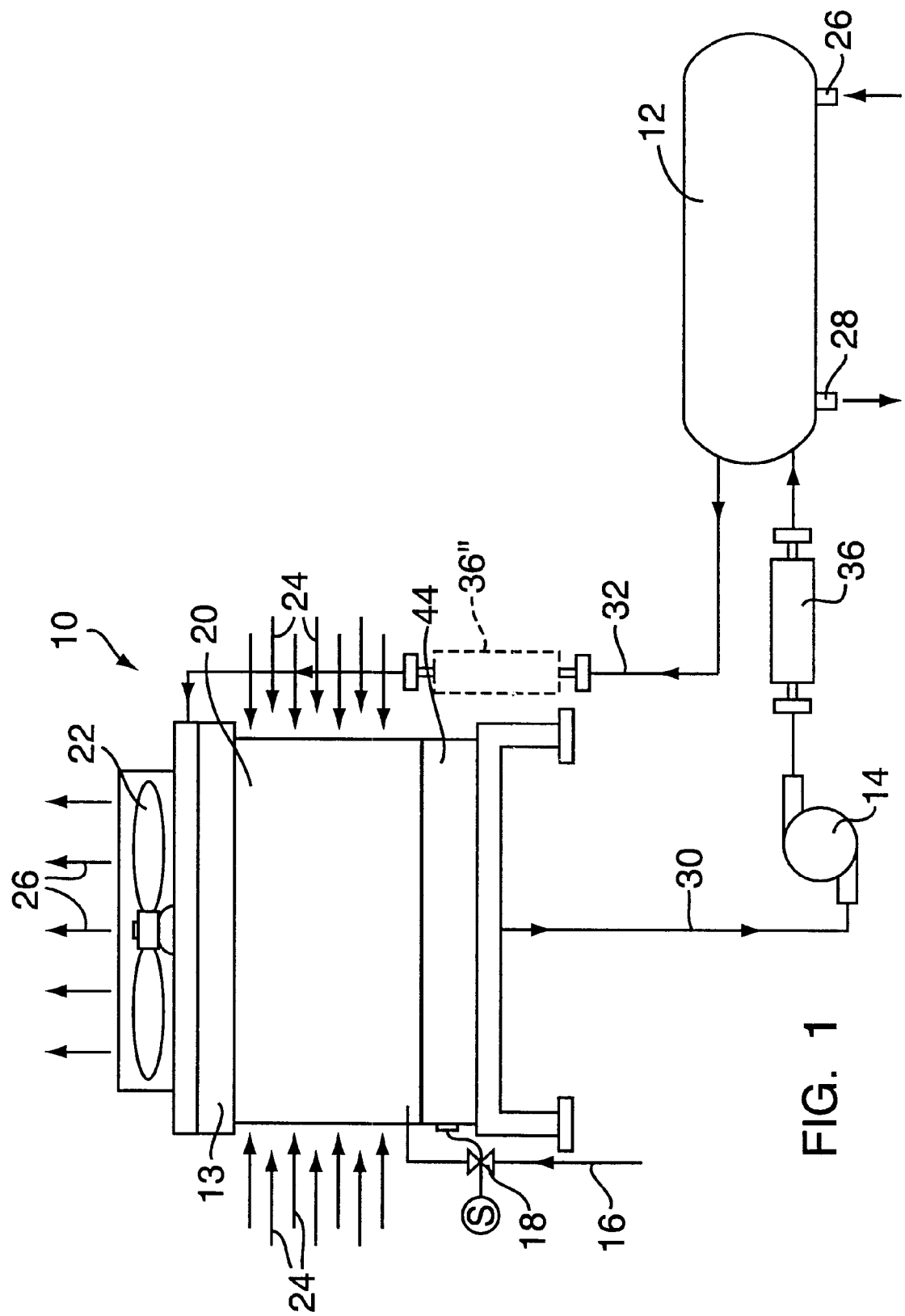
FIG. 1 A schematic illustration of a portion of an air conditioning system including a cooling tower to which the method of this invention is applied.

The present invention involves the previously unknown, unrecognized, and beneficial capability of being able to produce a stabilized oxidizing agent, believed to be a stabilized form of hydrogen peroxide, in water (or other liquid) by exposing the water to a certain type of varying magnetic flux when the water is in a certain condition in regard to concentration of dissolved oxygen and pH level. The method of the invention provides a cumulative build-up and maintenance of the oxidizing agent in the liquid which provides a distinct biocidal and/or biostatic and anti-biofilm effect. For discussion purposes only, as previously mentioned, the liquid to be treated is hereinafter often taken to be water, but the invention is not limited to just the treatment of water, and can be used to treat other liquids as well.

The method of the present invention comprises exposing water to bursts of ringing magnetic flux wherein the magnetic flux acts on the water to form a stabilized oxidizing agent. The ringing magnetic flux field may be provided by an apparatus such as that of U.S. Pat. No. 6,063,267 to Crewson et al. which issued on May 16, 2000, and is assigned to the assignee of the instant invention, and is herein incorporated by reference in its entirety. The magnetic flux generated and passed through the water by this apparatus is in the form of successive bursts or periods of ringing flux with the flux oscillations during the ringing periods being of relatively high primary frequency, such as 10 kHz to 80 kHz, plus harmonics, and with the ringing periods themselves being repeated at a frequency of between 1 Hz to 100 Hz, preferably 50 Hz to 60 Hz.

In the apparatus of U.S. Pat. No. 6,063,267, the circuit for producing successive bursts of ringing magnetic flux includes an inductor arrangement made up of one or more electrical coils which surround a pipe carrying the water to be treated. This inductor arrangement is connected to a 60 Hz electrical power source, at a voltage of about 5 V to 50 V (rms), through a switch in parallel with a small capacitance. At the beginning of each power supply cycle, the switch closes for about a quarter cycle so that current builds up in the inductor arrangement. When the switch is then suddenly opened, the supply current to the inductor arrangement is interrupted, causing the inductor arrangement to act in series with the capacitance to form a series resonant circuit with the supply voltage source, causing a decaying burst of ringing current to appear in the inductor arrangement, which ringing current has associated with it a corresponding ringing magnetic flux applied to the water in the pipe surrounded by the inductor.

The invention is not necessarily limited to use of the apparatus of U.S. Pat. No. 6,063,267 for the production of the required successive bursts or periods of ringing magnetic flux. Other apparatus can be used for such a purpose. In general, it is believed the ringing magnetic flux of the invention should have a primary frequency of 10 kHz to 80 kHz during each burst or ringing period, and the bursts or periods should repeat at a frequency of 1.0 Hz to 100 Hz preferably 50 Hz to 60 Hz. A dwell time equal to at least 4% to 20% of each repeat cycle should appear after each ringing burst or period.

As another means of generating the ringing flux, an inductor arrangement surrounding a water conducting pipe may be connected to an electrical power supply source, having an output primary frequency of about 10 kHz to 80 kHz, by way of a switch in series with the inductor arrangement and the power supply output terminals. An associated controller for the switch then alternately opens and closes the switch at a rate of 1.0 Hz to 100 Hz, preferably 50 Hz to 60 Hz, to provide periods or bursts of ringing current in the inductor arrangement and corresponding periods or bursts of ringing magnetic flux in the water.

The ringing magnetic flux in the inductor arrangement is used to generate the oxidizing agent in the water; thus, the water flow must be in close proximity to the ringing magnetic flux, and the pipe or other means holding the water must be made of plastic or other electrically non-conducting material such as to allow the magnetic flux to pass through it and into the water, so that a substantial portion of the magnetic flux passes directly through the water.

In accordance with the invention, it has been discovered that when water, having a significant amount of dissolved oxygen and a pH of 7 to 10, preferably 8 to 9, is exposed to a ringing magnetic flux of the character discussed above, an oxygen-bearing oxidizing agent having anti-microbial properties is produced. This oxidizing agent produces significant killing of, or major sub-lethal injury to, microorganisms present in the water, even if the microorganisms are ones which might form or already have formed biofilms or biofilm precursors.

An advantageous application of the present invention occurs in the context of an air conditioning cooling tower as shown, by way of example, in FIG. 1. This illustrated cooling tower is of a "cross-flow" design, but the invention is applicable to other types of cooling towers as well. Referring to FIG. 1, this figure shows a portion of an air conditioning system as typically installed in relatively large buildings such as apartment houses, office buildings, hospitals, and factories. The portion of the system illustrated includes a cooling tower, indicated generally at 10, a chiller 12, and a pump 14. The cooling tower 10 operates using a given body of water, some of which is maintained in an upper distribution or spraying chamber 13 and the major portion of which is maintained in a main tank 44. The amount of water comprising the body is kept within given maximum and minimum limits by adding make-up water as needed through a make-up water line 16 through a solenoid controlled valve 18 controlled by the level of the water in the main tank 44. Water flows from the upper chamber 13, to the main tank 44 over a plurality of evaporative fill material or honeycomb sheets 20, or the like, and at the same time a fan 22 moves ambient air over the sheets 20 to promote evaporation of the water. The arrows 24 indicate movement of ambient air into the cooling tower 10 and the arrows 26 indicate movement of that air out of the cooling tower 10.

The evaporation of water from the fill material or honeycomb sheets 20 cools the remaining, unevaporated water so that the water reaching and maintained in the main tank 44 is at a relatively low temperature.

The cold water in the tank 44 is used by the chiller 12 to cool a heat transfer medium which flows into the chiller 12 through an intake port 26 and out of the chiller through an outlet port 28. The cold water from the tank 44 is withdrawn from that tank by the pump 14 and supplied to the chiller 12 through a cold water line 30 and is returned, in warmed condition, from the chiller 12 to the upper chamber 13 of the cooling tower through a warm water line 32. The lines 30 and 32, the pump 14, the chiller 12, the top chamber 13, and the fill material or honeycomb sheets 20 therefore make up a flow path through which a portion of the water body is recirculated from and back to the main tank 44. Since this recirculated water is brought into intimate contact with ambient air as it passes over the sheets 20, the water in the main tank and passing through the lines 30 and 32 contains a significant amount of dissolved oxygen, such as 3 to 15 weight basis parts of oxygen per million parts of water, and preferably approximately 5 weight basis parts oxygen per million parts of water.

In keeping with the invention, in the cooling tower arrangement of FIG. 1 bursts of ringing magnetic flux are applied to the portion of the water which is recirculated from and back to the main tank 44. To accomplish this, as shown by the solid lines of FIG. 1, a ringing magnetic flux producing device 36 is included in the cold water line 30, with the device 36 preferably being one such as shown and described in U.S. Pat. No. 6,063,267. As an alternative to placement of the device 36 in the cold water line 30, it may alternatively be placed in the warm water line 32 as shown by the broken lines at '36. In either of the two alternative positions shown in FIG. 1, the water passing through the device 36 or '36 contains a significant amount of dissolved oxygen so that the device operates, among other things, to generate a stabilized form of hydrogen peroxide or other oxidizing agent in the water, thus consuming a significant part of the dissolved oxygen. Also, as previously mentioned, it is important that the water treated by the device 36 or '36 have a pH level somewhat above the neutral pH level of 7, the acceptable pH level being one within the range of pH 7 to pH 10, with the preferred range being that of pH 8 to pH 9. Fortunately, the application of bursts of ringing magnetic flux to the treated water, as accomplished by the illustrated device 36 or '36, have been found to usually inherently produce and maintain the pH level of the body of water in the cooling tower 10 at an acceptable pH level above neutral so that seldom, if ever, need any extra treatment of the water be made specifically for the purpose of adjusting its pH level.

As mentioned, a stable form or complex of hydrogen peroxide is believed to be the oxidizing agent produced by the method of this invention. In particular, it is believed that hydrogen peroxide is produced, either in the $H_2O_2$ non-ionized form or in the $HO_2^-$ ionized form, depending on pH, which then complexes to another ion or other complexing species found in the water to form a stabilized form or complex of hydrogen peroxide, the decomposition of which is delayed or occurs when it reacts with chemical components of a microbe. More specifically, after the hydrogen peroxide is produced by the bursts of ringing magnetic flux applied to the water the equilibrium equation for the relevant compounds, ions, and complexing species:

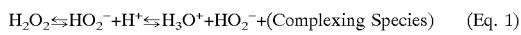
$$H_2O_2 \leftrightarrows HO_2^- + H^+ \leftrightarrows H_3O^+ + HO_2^- + (\text{Complexing Species}) \quad (\text{Eq. 1})$$

The $HO_2^-$ ions then join with complexing ions, or other complexing species which have either positive, negative or neutral changes, present in the water to form stable complexes, and the equilibrium equation between the $H_2O_2$ and these stable complexes becomes:

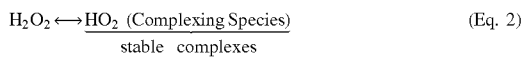
$$H_2O_2 \longleftrightarrow \underline{HO_2 \; (\text{Complexing Species})} \quad (\text{Eq. 2})$$
$$\text{stable complexes}$$

The hydrogen peroxide that is consumed by oxidizing bacteria is replenished by the operation of equilibrium in Equation 2. This has the effect of driving Equation 2 to the left, thus drawing more hydrogen peroxide out of storage from the stable complexes. Although pure hydrogen peroxide loses its anti-microbial effectiveness quickly due to decomposition, the ringing magnetic flux forms the stabilized hydrogen peroxide complex in the water upon the water's exposure to the ringing magnetic flux. Another oxidizing agent is ozone which has anti-microbial activity similar to that of hydrogen peroxide; and it is possible that a stabilized form of ozone, alone or in combination with a stabilized form of hydrogen peroxide, is an oxidizing agent formed by the broad method of this invention.

The formation of the oxidizing agent is enhanced when the water is aerated prior to exposure to the ringing magnetic field to provide dissolved oxygen in the water in a concentration of three (3) to fifteen (15) parts oxygen to a million parts water, by weight and preferably in a concentration of approximately five parts water to a million parts water, by weight. Aeration may be accomplished by any number of know mechanical means including cascades, sprays, and fill material or honeycomb plates for exposing large fluid surfaces to the atmosphere.

Figure 2:
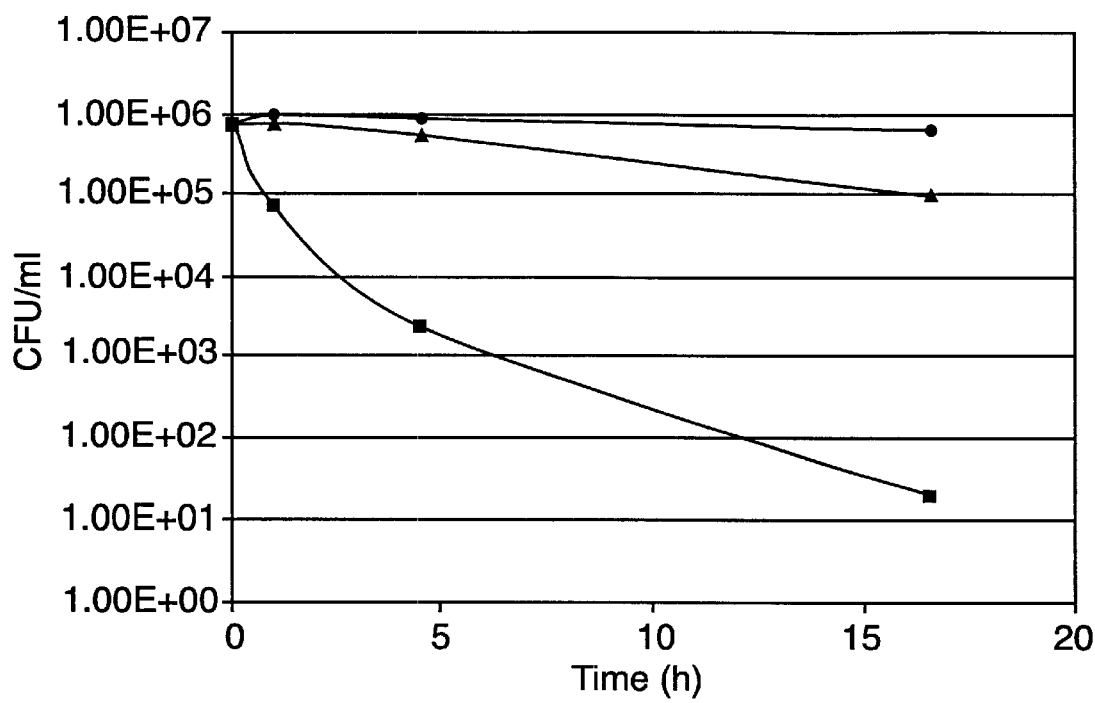
FIG. 2 A graph illustrating the anti-microbial effect of the ringing magnetic flux of this invention on *Enterobacter Cloacae* (*E. cloacae*).
Figure 3:
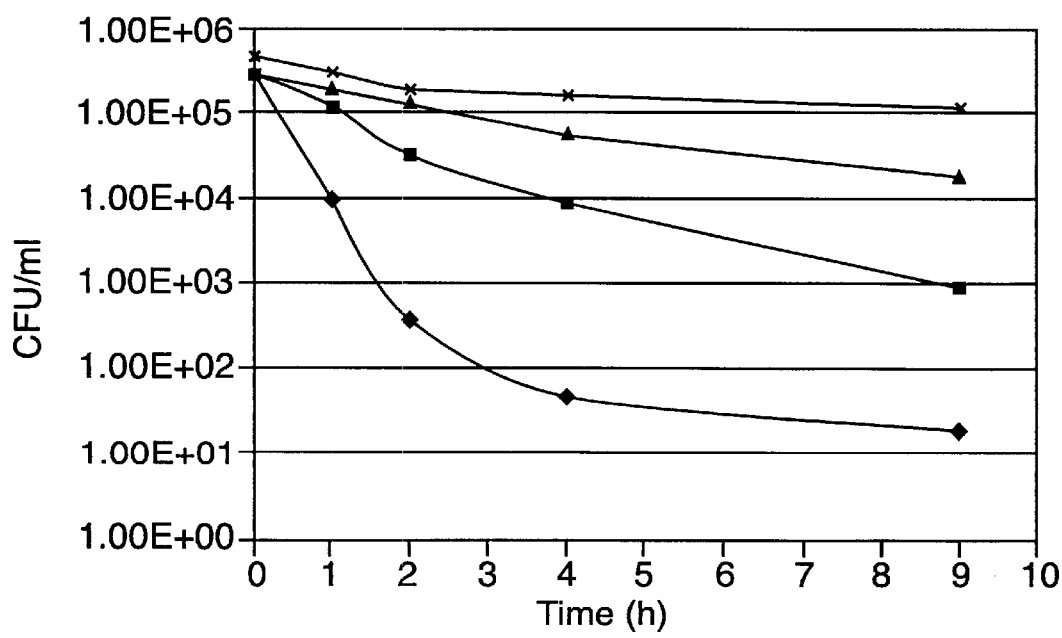
FIG. 3 A graph showing a comparison of the anti-microbial effects of water samples treated by the method of this invention at different pH levels.
Figure 4:
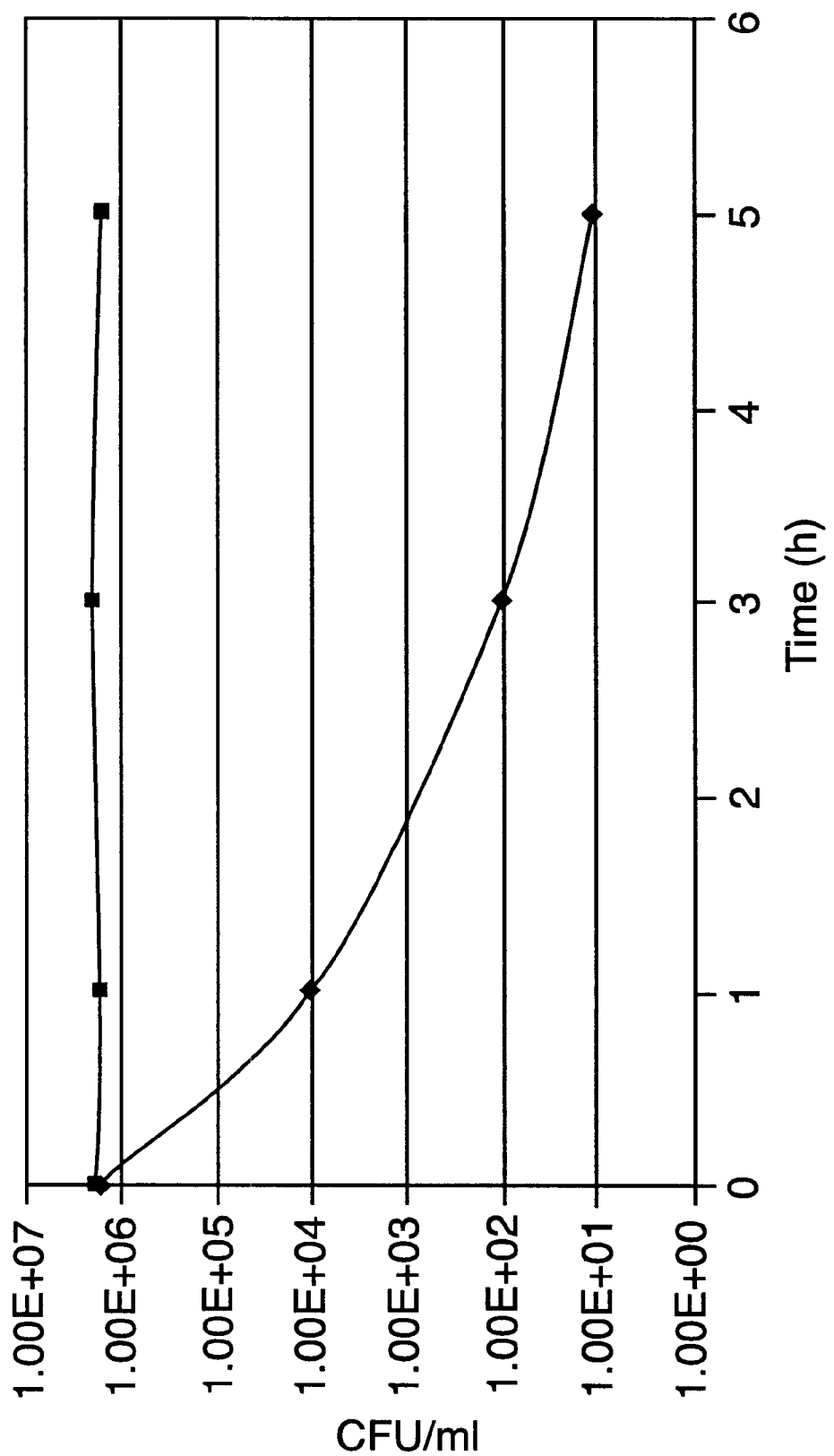
FIG. 4 A graph illustrating the effect of sodium thiosulfate on the oxidizing agent in water treated by the method of this invention.

Although different types of bacteria and other microorganisms are inactivated in water treated by the ringing magnetic flux of this invention, Gram negative bacteria appear to be more adversely effected than Gram positive bacteria. FIGS. 2 to 4 illustrate the unexpected anti-microbial effect of the ringing magnetic flux on *Enterobacter Cloacae* (*E. cloacae*), the presence of which indicates contamination of the water by fecal matter. FIG. 2 illustrates the inactivation of colony forming units of *E. cloacae* per milliliter (CFU/ml) over time. A water sample (—■—) having a prolonged exposure to the ringing magnetic flux of the invention so as to have an accumulation of the oxidizing agent, shows a significant decrease in the concentration of colony forming units in less than 24 hours. However, if sodium thiosulfate is added to such water to produce another water sample (—●—), there is little effect on the bacteria. Sodium thiosulfate reacts with any oxidizing agents present in the treated water to decompose or deactivate such oxidizing agents. These tests on the two samples (—■— and —●—), prove the concept that a stabilized oxidizing agent is formed in the water upon treatment with bursts of ringing magnetic flux. Comparatively, a water sample treated only with chlorine (—▲—) does not provide the same degree of deactivation of the colony forming units of *E. cloacae* as water treated with the ringing magnetic flux.

The killing activity of water treated with the ringing magnetic flux has unexpectedly been found to be pH dependent. The anti-microbial effect occurs most strongly when the water is slightly basic having a pH of about 8 to about 9. In FIG. 3, treated water samples at slightly basic pH and at about neutral pH are compared. The largest decrease in colony forming units of *E. cloacae* is present at a pH of 8.45 (—♦—). Bacteria would normally thrive in water at a pH of 8.45 without the treatment of the invention. As the pH decreases to neutral, the kill activity of the treated water decreases. At about a pH of 7.2 (—x—), there is only a slight drop in the number of colony forming units over time.

FIG. 4 again illustrates the effect of sodium thiosulfate on the oxidizing agent in the treated water. Water treated in accordance with the invention (—♦—) provides a significant decrease in the colony forming units of the *E. cloacae*. However, upon the addition of the sodium thiosulfate (—■—), the oxidizing agent is inactivated and, consequently, the number of colony forming units of the bacteria remain constant. Clearly, an oxidizing agent is formed in the water after exposure to the bursts of ringing magnetic flux.

The present invention achieves the objects stated above. Treating water with bursts of ringing magnetic flux generates an oxygen-rich stabilized oxidizing agent, such as a stabilized hydrogen peroxide, for simple, cost effective water treatment and purification. The stabilized oxidizing agent produced by the method of the invention significantly decreases colony forming units of bacteria and provides an efficient way of preventing, reducing and/or eliminating biofilms.

While the present invention has been particularly described in conjunction with specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. A method of making an oxidizing agent comprising the steps of:

providing a magnetic field in the form of successive bursts of ringing magnetic flux; and exposing a liquid to the bursts of magnetic flux for a period sufficient to form a stabilized oxidizing agent in a concentration sufficient to have a biocidal effect on miroorganisms in the liquid.

2. The method of claim 1 wherein:

in the step of exposing a liquid to the flux, the liquid comprises water.

3. The method of claim 1 wherein:

in the step of exposing a liquid to the flux, the stabilized oxidizing agent formed comprises a hydrogen peroxide complex.

4. The method of claim 1 further comprising the step of:

maintaining a body of the liquid; and wherein said step of exposing the liquid to the flux includes moving a portion of said liquid body through a recirculation flow path, and exposing the liquid moving through the recirculation flow path to the flux.

5. The method of claim 4 wherein:

the step of exposing the liquid moving through the recirculation flow path to the flux is continued for a substantial amount of time to cause the stabilized oxidizing agent to accumulate uniformly in the liquid body.

6. The method of claim 5 further including the step of:

aerating said portion of the liquid body as said portion moves through the recirculation flow path.

7. The method of claim 6 further including the step of:

maintaining the pH of the liquid body at a level of 7 to 10.

8. The method of claim 1 further including the step of:

aerating the liquid prior to exposing the liquid to the flux.

9. The method of claim 1 wherein:

the steps of providing a magnetic field and exposing the liquid to the flux comprises passing the liquid through an apparatus which generates a ringing magnetic flux pattern in which ringing magnetic flux appears in successive ringing periods with flux oscillations during a ringing period being of a frequency between 10 kHz and 80 kHz, and in which the ringing periods are repeated at a frequency of 1 Hz to 100 Hz.

10. A method of forming a stabilized oxidizing agent in water comprising the steps of:

aerating the water to provide dissolved oxygen in the water;

producing bursts of ringing magnetic flux having a frequency of 10 kHz to 80 kHz during each burst and with the bursts being repeated at a frequency of 1 Hz to 100 Hz; and exposing the aerated water to the bursts of ringing magnetic flux for a period sufficient to form a stabilizing oxidizing agent.

11. The method of claim 10 wherein:

in the step of exposing the aerated water to the flux, the stabilized oxidizing agent formed comprises a form of hydrogen peroxide.

12. The method of claim 10 further including the step of:

maintaining a body of the water and holding a main portion of said body of water in a main tank; and wherein said step of exposing the aerated water to the magnetic flux comprises recirculating a portion of the body of water to and from the main tank through a recirculation flow path, and exposing the portion of the water moving through the recirculation path to the magnetic flux.

13. The method of claim 12, wherein:

said step of aerating the water is such as to maintain the dissolved oxygen in the body of water at level greater than 3 parts oxygen by weight to one million parts water by weight.

14. The method of claim 13, further comprising:

maintaining a pH level of 7 to 10 in said body of water.

15. The method of claim 14, further comprising the step of:

maintaining a pH level of 8 to 9 in said body of water.

16. A method of treating water in an air conditioning system cooling tower having a water evaporation means with water evaporation surfaces from which water evaporates into air moved past the evaporation surfaces, a water inlet, a distribution means for distributing water received through the water inlet onto the evaporation surfaces, a main tank for receiving water moving from the evaporation surfaces, a water outlet for removing water from the main tank, and means providing a recirculation flow path for recirculating water from said outlet to said inlet, said method comprising:

moving water through said recirculation flow path, producing bursts of ringing magnetic flux in the water moved through said recirculation flow and having a frequency of 10 kHz to 80 kHz during each burst of ringing flux with the bursts of ringing flux being repeated at a frequency of 1 Hz to 100 Hz to form a stabilized oxidizing agent in the water which oxidizing agent has an anti-microbial effect involving oxidation of the oxidizing agent with chemical components of microorganisms in the water.

* * * * *